United States Patent
Sherman

(10) Patent No.: US 6,555,135 B1
(45) Date of Patent: Apr. 29, 2003

(54) PHARMACEUTICAL COMPOSITIONS COMPRISING CO-MICRONIZED FENOFIBRATE

(75) Inventor: Bernard Charles Sherman, 50 Old Colony Road, Willowdale, Ontario (CA), M2L 2K1

(73) Assignee: Bernard Charles Sherman, Toronto (CA)

( * ) Notice: Subject to any disclaimer, the term of this patent is extended or adjusted under 35 U.S.C. 154(b) by 0 days.

(21) Appl. No.: 09/544,498

(22) Filed: Apr. 7, 2000

(30) Foreign Application Priority Data

Apr. 27, 1999 (CA) ................................................ 2270306

(51) Int. Cl.⁷ .................................................. A61K 9/20
(52) U.S. Cl. ........................ 424/464; 424/400; 424/489; 514/951; 514/960
(58) Field of Search ................................. 424/449, 451, 424/452, 455, 456, 458, 462, 489; 514/49, 458, 340, 342, 543, 544, 548, 569

(56) References Cited

U.S. PATENT DOCUMENTS

| 4,895,726 A | | 1/1990 | Curtet et al. | |
|---|---|---|---|---|
| 5,827,536 A | * | 10/1998 | Laruelle | 424/451 |
| 5,880,148 A | * | 3/1999 | Edgar et al. | 514/458 |
| 6,074,670 A | * | 6/2000 | Stamm et al. | 424/462 |
| 6,124,358 A | * | 9/2000 | Estanove et al. | 514/548 |

FOREIGN PATENT DOCUMENTS

CA 2214895 4/1989

* cited by examiner

Primary Examiner—Carlos Azpuru
Assistant Examiner—Charesse Evans
(74) Attorney, Agent, or Firm—Neil H. Hughes; Ivor M. Hughes; Marcelo K. Sarkis

(57) ABSTRACT

A pharmaceutical composition for oral administration comprising a co-micronized mixture of fenofibrate and a solid excipient that is not a surfactant.

8 Claims, No Drawings

PHARMACEUTICAL COMPOSITIONS COMPRISING CO-MICRONIZED FENOFIBRATE

FIELD OF INVENTION

The present invention relates to pharmaceutical compositions for oral administration comprising fenofibrate which enable improve dissolution and bioavailability.

BACKGROUND

Fenofibrate is practically insoluble in water. This causes fenofibrate to exhibit a low rate of dissolution in aqueous media (including gastrointestinal fluids). Which results in inadequate bioavailability (absorption into systemic circulation) after oral ingestion.

In order to make a composition comprising fenofibrate that will enable maximum bioavailability, it is necessary to incorporate into the composition a feature that increases the rate of dissolution of the drug in gastrointestinal fluids.

Several ways of increasing the rate of dissolution of drugs having low solubility in water are known in the prior art.

One approach is micronization. In this approach, the drug is milled to fine particles, typically having a mean diameter of under about 15 microns. A second approach is to include a surfactant in the composition.

For the drug fenofibrate, neither micronization alone nor use of a surfactant alone enables maximum bioavailability. U.S. Pat. No. 4,895,726 discloses that the rate of dissolution and the bioavailability of fenofibrate can be maximized by co-micronization of fenofibrate with a solid surfactant. In this process the fenofibrate is first mixed with the solid surfactant and then the mixture is micronized.

A composition made according to the invention of U.S. Pat. No. 4,895,726 is sold in Canada under the tradename Lipidil Micro and in the United States under the tradename Tricor. A disadvantage of the technology of U.S. Pat. No. 4,895,726 is the need to include the solid surfactant in the composition. Because of the toxicity of surfactants, it is preferable to avoid use of a surfactant if possible. Another method of increasing the dissolution rate of fenofibrate is disclosed in Canadian patent application No. 2214895. This publication discloses that the bioavailability of fenofibrate can be improved by making a solid dispersion of a disintegrant in the fenofibrate. This is done by melting the fenofibrate, blending the disintegrant into the molten fenofibrate, and resolidifying the mixture. The resulting solid can then be ground up into granules and the granules used to make the final composition. For example, the granules can be filled into two-piece hard gelatin capsules.

A disadvantage of the method of Canadian patent application No. 2214895 is that it requires the use of specialized equipment to make the molten blend.

In view of the limitations of the prior art, it is the object of the present invention to enable increased dissolution rate of fenofibrate without the need to incorporate a surfactant in the composition, and without the need to make a molten blend.

DESCRIPTION OF THE INVENTION

It has been found that the dissolution rate of fenofibrate can be substantially increased by co-micronization of fenofibrate with a pharmaceutically acceptable excipient that is not a surfactant. This is surprising in light of the U.S. Pat. No. 4,895,726 which teaches co-micronization only with a solid surfactant.

The term "pharmaceutically acceptable excipient" will be understood to mean any ingredient having no therapeutic activity and being nontoxic and thus suitable as an excipient.

Suitable excipients will include any of the excipients commonly used in pharmaceutical products, such as, for example, microcrystalline cellulose, lactose and starch, provided that such excipient is solid at room temperature and not a surfactant.

The ratio of the weight of the excipient to the weight to fenofibrate may be anywhere from about 1:100 to about 2:1, will preferably be from about 1:10 to about 3:2, and will most preferably be about 1:1.

The co-micronization of the fenofibrate and excipient will advantageously be carried out by mixing the fenofibrate and excipient together and then micronizing of the mixture on conventional micronization equipment, such as an air-jet mill. The mixture will preferably be micronized such that the mean particle size is less than 15 microns, more preferably less than 10 microns, and most preferably less than 5 microns.

The co-micronized powder may then be processed into solid dosage forms for oral administration (i.e. tablets or capsules).

This may be, for example, in one of the following ways:
1. Filling the co-micronized powder directly into 2-piece hard gelatin capsules.
2. Mixing the co-micronized powder with other excipients, such as, for example, fillers, binders, disintegrants, lubricants and glidants, and either filling the mixture into 2-piece hard gelatin capsules or compressing the mixture into tablets.

The invention will be more clearly understood from the following examples.

EXAMPLE 1

500 g of fenofibrate was mixed with 500 g of lactose monohydrate powder, and the mixture was micronized on an air-jet mill. 2 piece hard gelatin capsules were then filled with the resultant co-micronized powder to a net fill weight of 400 mg per capsule, so that each capsule contained 200 mg of fenofibrate.

EXAMPLE 2

500 g of fenofibrate was mixed with 500 g of microcrystalline cellulose, and the mixture was micronized on an air-jet mill. 2-piece hard gelatin capsules were then filled with the resultant co-micronized powder to a net fill weight of 400 mg per capsule, so that each capsule contained 200 mg of fenofibrate.

EXAMPLE 3

For comparison purposes, a quantity of pure fenofibrate was micronized using the same air-jet mill.

A sample of the pure micronized fenofibrate was then mixed with an equal weight of lactose monohydrate power. 2-piece hard gelatin capsules were then filled with the resultant mixture to a net fill weight of 400 mg per capsule, so that each capsule again contained 200 mg of fenofibrate.

Dissolution Results

Capsules of examples 1 and 2 were compared to capsules of example 3 for dissolution rate.

The equipment used for dissolution testing was United States Pharmacopoeia Apparatus #2. The paddle speed was 100 rpm, and the medium was 900 mL of 0.1N sodium dodecyl sulfate water.

It was found that, in 60 minutes, over 90% was dissolved from the capsules of examples 1 and 2, whereas only 50% to 70% was dissolved for the capsules of example 3.

It is thus clear that the dissolution rate is substantially higher using fenofibrate that has been co-micronized with a solid excipient such as lactose or microcrystalline cellulose, in comparison to fenofibrate that has been micronized in pure form and then mixed with a solid excipient.

What is claimed is:

1. A pharmaceutical composition comprising a comicronized mixture of fenofibrate, and a solid non-toxic amount of a pharmaceutically acceptable excipient having no therapeutic activity that is not a surfactant.

2. The composition of claim 1 wherein the mean particle size of the said comicronized mixture is less than 15 microns.

3. The composition of claim 1 wherein the mean particle size of the said comicronized mixture is less than 10 microns.

4. The composition of claim 1 wherein the mean particle size of the said comicronized mixture is less than 5 microns.

5. The composition of claim 1 wherein the ratio of the excipient to fenofibrate by weight is from about 1:100 to about 2:1.

6. The composition of claim 1 wherein the ratio of the excipient to fenofibrate by weight is about 1:10 to about 3:2.

7. The composition of claim 1 wherein the ratio of the excipient to fenofibrate by weight is about 1:1.

8. The composition of claim 1 wherein the excipient is selected from the group consisting of microcrystalline cellulose, lactose, and starch.

* * * * *